(12) United States Patent
Luo et al.

(10) Patent No.: US 6,346,555 B1
(45) Date of Patent: Feb. 12, 2002

(54) PROCESS AND CATALYST FOR PREPARING $C_2$-OXYGENATES FROM SYNTHESIS GAS

(75) Inventors: Hongyuan Luo; Huanwen Zhou, both of Dalian (CN)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/598,244

(22) Filed: Jun. 21, 2000

(30) Foreign Application Priority Data

Jun. 25, 1999 (DE) .......................................... 199 29 281

(51) Int. Cl.⁷ .............................................. C07C 27/00
(52) U.S. Cl. ........................ 518/713; 518/716; 518/714
(58) Field of Search ................................ 518/713, 716, 518/714

(56) References Cited

U.S. PATENT DOCUMENTS 4,492,772 A * 1/1985 Ball et al. ................... 518/713

FOREIGN PATENT DOCUMENTS

| EP | 010 295 A1 | 4/1980 |
|---|---|---|
| EP | 079 132 A1 | 5/1983 |
| JP | 9078 130 | 5/1984 |

* cited by examiner

*Primary Examiner*—Samuel Barts
(74) *Attorney, Agent, or Firm*—Keil & Weinkauf

(57) ABSTRACT

In a process for preparing $C_2$-oxygenates by reaction of CO and $H_2$ over a rhodium-containing supported catalyst, the catalyst comprises, based on the total weight, from 0.01 to 10% by weight of rhodium,
    from 0.001 to 10% by weight of zirconium,
    from 0.01 to 5% by weight of iridium,
    from 0.01 to 10% by weight of at least one metal selected from among copper, cobalt, nickel, manganese, iron, ruthenium and molybdenum,
    from 0.01 to 10% by weight of at least one alkali metal or alkaline earth metal selected from among lithium, sodium, potassium, rubidium, magnesium and calcium, on an inert support.

6 Claims, No Drawings

PROCESS AND CATALYST FOR PREPARING C$_2$-OXYGENATES FROM SYNTHESIS GAS

The invention relates to a process and a catalyst for preparing C$_2$-oxygenates from synthesis gas, i.e. CO/H$_2$ gas mixtures.

The heterogeneously catalyzed conversion of synthesis gas into hydrocarbons (Fischer-Tropsch synthesis) or into methanol has been known since the 1920s. It was discovered only in 1975 that rhodium catalysts can convert synthesis gas directly into C$_2$-oxygenates.

In principle, the direct reaction of synthesis gas over rhodium catalysts can lead to a broad range of products. Thus, methane and higher hydrocarbons and also oxygenates such as methanol, ethanol, higher alcohols, diols, acetaldehyde and acetic acid are formed over unpromoted Rh/SiO$_2$ catalysts. Both the selectivity and the activity of rhodium catalysts can be considerably modified by doping with other elements or by appropriate selection of the support. For example, doping with lithium or potassium serves to suppress methane formation, doping with manganese gives a considerable increase in activity without the selectivity being significantly influenced, and the use of CeO$_2$ instead of SiO$_2$ as support results in a significant increase in the selectivity of ethanol formation. Furthermore, the product distribution depends on reaction parameters such as pressure, temperature, conversion and CO/H$_2$ ratio.

EP-A-0 010 295 describes a process for preparing ethanol from synthesis gas, in which the reaction is carried out over a supported rhodium catalyst comprising, as cocatalyst, one or more of the elements zirconium, hafnium, lanthanum, platinum, chromium and mercury.

EP-A-0 079 132 relates to a process for preparing oxygenated hydrocarbons by catalytic reaction of synthesis gas over a supported catalyst comprising, as active components, rhodium, silver, zirconium and molybdenum and also, if desired, iron, manganese, rhenium, tungsten, ruthenium, chromium, thorium and potassium. The preferred support material is silicon dioxide.

J5 9078-130-A relates to a process for preparing acetic acid, acetaldehyde and ethanol by reaction of synthesis gas over a rhodium catalyst comprising manganese, zirconium and at least one alkali metal as promoters.

The direct, heterogeneously catalyzed gas-phase synthesis of acetic acid from synthesis gas over rhodium catalysts has been intensively researched, especially in the years 1980 to 1986 as part of the Japanese C$_1$ project "Research and Development Program for New Technologies to Produce Basic Industrial Chemicals from Carbon Monoxide and other Chemicals". During the course of this work on the synthesis of acetic acid, the influence of about 60 elements as promoters on the activity and selectivity of heterogeneous rhodium catalysts was systematically examined. It was found that promoters such as Mg, Sc, Ti, V, Cr, Mn, Mo or La increase the catalytic activity, while promoters such as Li, K, Zr or Ir lead to an increase in the selectivity of acetic acid formation. At the end of the project, an optimized Rh—Mn—Ir—Li—K/SiO$_2$ catalyst enabled an acetic acid selectivity of 71% to be achieved at a space-time yield of 344 g/l*h. A further catalyst which was not described in more detail but gave an overall selectivity to acetic acid+ acetaldehyde of 90% at a space-time yield of 480 g/l*h was also developed.

The results of the Japanese C$_1$ project have been compiled in the book "Progress in C$_1$ Chemistry in Japan", Elsevier, 1989, with specifically the work on the preparation of acetic acid from synthesis gas being described in Chapter 6 (pages 287 to 330). In the screening tests on catalyst optimization, not only was the influence of various promoters on the catalyst performance elucidated, but a number of further parameters such as the test conditions (P, T, SV, CO/H$_2$ ratio), partial poisoning with sulfur, the support composition and pore structure, the Rh particle size and the conditions in the drying and the reduction of the catalyst were also examined. In addition, the reaction kinetics over an Rh—Mn—Ir—Li—K/SiO$_2$ catalyst and the ageing behavior of an Rh—Mn—Ir—Li/SiO$_2$ catalyst were examined.

It is an object of the present invention to provide a process and a catalyst for preparing C$_2$-oxygenates, which give the desired products with high conversions and high selectivities at a high catalyst activity and operating life.

We have found that this object is achieved by a process for preparing C$_2$-oxygenates by reaction of CO and H$_2$ over a rhodium-containing supported catalyst, in which the catalyst comprises, based on the total weight, from 0.01 to 10% by weight of rhodium, from 0.001 to 10% by weight of zirconium, from 0.01 to 5% by weight of iridium, from 0.01 to 10% by weight of at least one metal selected from among copper, cobalt, nickel, manganese, iron, ruthenium and molybdenum, from 0.01 to 10% by weight of at least one alkali metal or alkaline earth metal selected from among lithium, sodium, potassium, rubidium, magnesium and calcium, on an inert support.

It has been found, according to the present invention, that the above catalyst displays a very good performance spectrum in the conversion of synthesis gas into C$_2$-oxygenates. The catalyst displays a high activity and selectivity, even when the rhodium content is very low.

The catalyst support is preferably selected from among SiO$_2$, Al$_2$O$_3$, TiO$_2$, zeolites, activated carbon, diatomaceous earth and mixtures thereof.

The alkali or alkaline earth metal or metals is/are preferably selected from among lithium, potassium and magnesium.

The metal or metals is/are preferably selected from among copper, manganese, iron, ruthenium and molybdenum.

A preferred catalyst comprises from 0.1 to 5% by weight, in particular from 0.5 to 3.5% by weight, of rhodium, from 0.05 to 5% by weight, in particular form 0.08 to 4.5% by weight, of zirconium, from 0.1 to 3.5% by weight, in particular from 0.2 to 2.5% by weight, of iridium, from 0.1 to 5% by weight, in particular from 0.2 to 1.5% by weight, of at least one metal selected from among copper, cobalt, nickel, manganese, iron, ruthenium and molybdenum, from 0.05 to 5% by weight, in particular from 0.1 to 1.2% by weight, of at least one alkali metal or alkaline earth metal selected from among lithium, sodium, potassium, rubidium, magnesium and calcium, on an inert support.

The catalyst of the present invention can be obtained by impregnating the inert support with catalyst metal compounds, in particular catalyst metal salts, dissolved in aqueous or organic solvents, drying and calcining the impregnated support and subsequently reducing it. The impregnation can be carried out in any desired manner, for example by steeping or spraying. Preference is given to using catalyst metal salts which are soluble in water or organic solvents such as ethanol. The order in which the support is impregnated with the catalyst metal compounds can be chosen freely. Impregnation can be carried out successively or simultaneously with all components.

According to the present invention, the catalyst is used in the reaction of synthesis gas, in particular to give $C_2$-oxygenates such as ethanol, acetaldehyde and acetic acid.

The reaction is preferably carried out at a pressure in the range from 1 to 100 bar and at a temperature in the range from 200 to 400° C.

The molar ratio of $H_2$ to CO is preferably 10–0.05:1.

The invention is illustrated by the examples below.

EXAMPLE 1

$RhCl_3$, $ZrO(NO_3)_2$, $H_2IrCl_6$, $Cu(NO_3)_2$ and $KNO_3$ were dissolved in water in amounts corresponding to the desired concentration ratio on the support. The support ($SiO_2$, 20–40 μm) was then dipped into the solution for from 1 to 2 hours. After removal from the solution and allowing excess solution to drip off, the support was dried at from 50 to 60° C. for 24 hours and subsequently calcined at 110° C. for 6 hours. The catalyst obtained contained 1.5% by weight of Rh, 0.1% by weight of Zr, 0.3% by weight of Ir, 0.8% by weight of Cu and 0.2% by weight of K.

Prior to the reaction with synthesis gas, the catalyst was reduced with hydrogen for 3 hours at 300° C. Synthesis gas was then reacted at a temperature of 300° C. The total pressure of CO and $H_2$ was 3.0 MPa, the molar ratio of $H_2$/CO was 2. The space velocity was 15,000 $h^{-1}$.

The CO conversion was 4.5%, the space-time yield of $C_2$-oxygenates was 312.6 g/kg h. The selectivity was 70.1% of CO.

EXAMPLE 2

The same catalyst as in Example 1 was used, but in its preparation the support was first dipped into $ZrO(NO_3)_2$ solution, subsequently dried and then dipped into a solution comprising $RhCl_3$, $H_2IrCl_6$, $Cu(NO_3)_2$ and $KNO_3$. The catalyst was then The CO conversion was 4.3%, the space-time yield of $C_2$-oxygenates was 351.2 g/kg h. The selectivity was 73.5% of CO.

EXAMPLES 3 to 11

The reaction was carried out as described in Example 1, but the catalyst indicated in the following table was used. The results are shown in the following table.

| Example | Catalyst | CO conversion % | Space-time yield of $C_2$-oxygenates | C2-oxy selectivity % (C) |
|---|---|---|---|---|
| 3 | 3.5Rh—0.2Zr—0.2Ir—0.7Cu—0.1Li/SiO$_2$ | 8.7 | 726.8 | 75.8 |
| 4 | 1Rh—0.08Zr—0.5Ir—0.5Mn—0.8K—0.1L/SiO$_2$ | 3.4 | 273.5 | 69.2 |
| 5 | 1.5Rh—0.1Zr—0.Ir—0.2Fe—0.1Ru—0.2K/SiO$_2$ | 4.8 | 414.9 | 77.8 |
| 6 | 2.0Rh—0.1Zr—1.0Ir—0.2Ru—0.5Li/SiO$_2$ | 5.4 | 440.2 | 73.2 |
| 7 | 0.5Rh—0.3Zr—0.8Ir—0.9Ru—0.3Mo—0.2Mg/ZSM-5 | 2.1 | 148.6 | 63.7 |
| 8 | 1.0Rh—2.8Zr—0.2Ir—1.0Mn—0.5Mo—1.2Li/SiO$_2$ | 4.2 | 336.5 | 72.1 |
| 9 | 1.0Rh—4.5Zr—0.5Ir—0.5Mn—0.5Cu—0.8K/SiO$_2$ | 3.9 | 340.2 | 78.5 |
| 10 | 1.0Rh—0.3Zr—2.5Ir—0.5Mn—0.2K/SiO$_2$ | 4.2 | 363.5 | 77.9 |
| 11 | 1.0Rh—0.3Zr—2.5Ir—0.5Mn—0.2K/Al$_2$O$_3$ | 5.9 | 362.1 | 55.7 |
| C1 | 1.0Rh—0.5Mn—0.2K/SiO$_2$ | 1.2 | 96.7 | 65.3 |
| C2 | 1.0Rh—2.5Ir—5Mn—2K/SiO$_2$ | 3.9 | 289.4 | 66.8 |

We claim:

1. A process for preparing $C_2$-oxygenates by reaction of CO and $H_2$ over a rhodium-containing supported catalyst, in which the catalyst consists essentially of, based on the total weight, from 0.01 to 10% by weight of rhodium, from 0.001 to 10% by weight of zirconium, from 0.01 to 5% by weight of iridium, from 0.01 to 10% by weight of at least one metal selected from among copper, cobalt, nickel, manganese, iron, ruthenium and molybdenum, from 0.01 to 10% by weight of at least one alkali metal or alkaline earth metal selected from among lithium, sodium, potassium, rubidium, magnesium and calcium, on an inert support.

2. A process as claimed in claim 1, wherein the catalyst support is selected from among $SiO_2$, $Al_2O_3$, $TiO_2$, zeolites, activated carbon and diatomaceous earth.

3. A process as claimed in claim 1, wherein the alkali or alkaline earth metal or metals is/are selected from among lithium, potassium and magnesium.

4. A process as claimed in claim 1, wherein the metal or metals is/are selected from among copper, manganese, iron, ruthenium and molybdenum.

5. A process as claimed in claim 1, wherein the reaction is carried out at a pressure in the range from 1 to 100 bar and at a temperature in the range from 200 to 400° C.

6. A process as claimed in claim 1, wherein the molar ratio of $H_2$ to CO is 10–0.05:1.

* * * * *